United States Patent
Singh et al.

(10) Patent No.: US 12,406,751 B2
(45) Date of Patent: Sep. 2, 2025

(54) FLUID LOSS REQUIREMENT OF A CEMENT SLURRY USING BULK BLEND MATERIALS

(71) Applicant: Halliburton Energy Services, Inc., Houston, TX (US)

(72) Inventors: John Paul Bir Singh, Kingwood, TX (US); Siva Rama Krishna Jandhyala, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 995 days.

(21) Appl. No.: 17/500,116

(22) Filed: Oct. 13, 2021

(65) Prior Publication Data

US 2023/0111521 A1 Apr. 13, 2023

(51) Int. Cl.
  *G16C 20/30* (2019.01)
  *C09K 8/487* (2006.01)
  *G16C 20/70* (2019.01)

(52) U.S. Cl.
  CPC .............. *G16C 20/30* (2019.02); *C09K 8/487* (2013.01); *G16C 20/70* (2019.02)

(58) Field of Classification Search
  CPC ......... G16C 20/30; G16C 20/70; C09K 8/487
  See application file for complete search history.

(56) References Cited

U.S. PATENT DOCUMENTS

| | | | |
|---|---|---|---|
| 6,739,806 B1 | 5/2004 | Szymanski et al. | |
| 11,643,587 B2* | 5/2023 | Boul | C09K 8/467 523/130 |
| 11,820,708 B2* | 11/2023 | Alanqari | C04B 24/121 |
| 2007/0101905 A1 | 5/2007 | Chatterji et al. | |
| 2007/0284105 A1 | 12/2007 | Beckman | |
| 2017/0364607 A1 | 12/2017 | Kaushik et al. | |
| 2020/0299564 A1* | 9/2020 | Lin | C04B 20/0004 |
| 2021/0147742 A1 | 5/2021 | Pearl, Jr. et al. | |
| 2021/0150104 A1 | 5/2021 | Singh et al. | |
| 2021/0207016 A1* | 7/2021 | Michaux | C04B 24/20 |
| 2022/0242786 A1* | 8/2022 | Shanmugam | C08F 293/005 |

(Continued)

FOREIGN PATENT DOCUMENTS

| EP | 0832861 B1 | 7/2001 |
|---|---|---|
| WO | 2020-204958 | 10/2020 |

OTHER PUBLICATIONS

Baris Alp et al.; "Utilization of supplementary cementitious materials in geothermal well cementing"; Proceedings, Thirty-Eighth Workshop on Geothermal Reservoir Engineering Stanford University, Stanford, California, Feb. 11-13, 2013 (Year: 2013).*

(Continued)

*Primary Examiner* — Nithya J. Moll
*Assistant Examiner* — Nupur Debnath
(74) *Attorney, Agent, or Firm* — Thomas Rooney; C. Tumey Law Group PLLC

(57) ABSTRACT

A method may include providing a fluid loss model, providing a fluid loss requirement, generating a cement slurry recipe using the fluid loss model and the fluid loss requirement such that a calculated fluid loss of the cement slurry recipe using the fluid loss model meets or exceeds the fluid loss requirement; and preparing a cement slurry based on the cement slurry recipe.

17 Claims, 6 Drawing Sheets

(56) References Cited

U.S. PATENT DOCUMENTS

2022/0259482 A1* 8/2022 Alkhalaf ............... C09K 8/467

OTHER PUBLICATIONS

Ikpeka Princewill Maduabuchi et al.; "Effects of Additive Concentrations on Cement Rheology at Different Temperature Conditions"; International Journal of Engineering Works; vol. 6, Issue 03, pp. 50-70, Mar. 2019 (Year: 2019).*
International Search Report and Written Opinion for Application No. PCT/US2022/039816, dated Nov. 28, 2022.
U.S. Appl. No. 16/923,718, filed Jul. 8, 2020.
U.S. Appl. No. 16/923,752, filed Jul. 8, 2020.
U.S. Appl. No. 16/923,797, filed Jul. 8, 2020.
European Patent Office Extended European Search Report for EP Application No. 22881522.1 dated Apr. 15, 2025. PDF file. 20 pages.
Vipulanandan, C. et al. "Effect of drilling mud bentonite contents on the fluid loss and filter cake formation on a field clay soil formation compared to the API fluid loss method and characterized using Vipulanandan models." The Journal of Petroleum Science and Engineering, vol. 189, Feb. 2020, pp. 1-13. PDF file. 13 pages.

* cited by examiner

FLUID LOSS REQUIREMENT OF A CEMENT SLURRY USING BULK BLEND MATERIALS

BACKGROUND

In well cementing, such as well construction and remedial cementing, cement slurries are commonly utilized. Cement slurries may be used in a variety of subterranean applications. For example, in subterranean well construction, a pipe string (e.g., casing, liners, expandable tubulars, etc.) may be run into a well bore and cemented in place. The process of cementing the pipe string in place is commonly referred to as "primary cementing." In a typical primary cementing method, a cement slurry may be pumped into an annulus between the walls of the well bore and the exterior surface of the pipe string disposed therein. The cement slurry may set in the annular space, thereby forming an annular sheath of hardened, substantially impermeable cement (i.e., a cement sheath) that may support and position the pipe string in the well bore and may bond the exterior surface of the pipe string to the subterranean formation. Among other things, the cement sheath surrounding the pipe string functions to prevent the migration of fluids in the annulus, as well as protecting the pipe string from corrosion. Cement slurries also may be used in remedial cementing methods, for example, to seal cracks or holes in pipe strings or cement sheaths, to seal highly permeable formation zones or fractures, to place a cement plug, and the like.

A particular challenge in cementing may be to retain satisfactory slurry performance throughout the cementing operation. Oftentimes, a polymer is added to the cement slurry such that a consistent fluid volume within the cement slurry may be maintained. A polymer may reduce the loss of water through a cement filter cake from the wellbore being cemented into the formation or other permeable zones penetrated by the wellbore. The loss of water from the cement slurry may have many deleterious effects on the cement including changes in density viscosity and thickening time as well as changes in compressive strength of the set cement among other factors. In extreme circumstances, fluid loss may increase the equivalent circulating density which may lead to formation fracture and lost circulation or flash setting of the slurry. Poor fluid loss control has been recognized in the industry as contributing to excessive density increase and annulus bridging and has been found to be a factor in some primary cementing failures. Predictability of slurry properties during pumping of the slurry and the mechanical properties of the final set cement are typically the most important parameters in a cementing operation. The oilfield industry has made considerable advances in control over slurry properties during mixing by development of polymers that increase predictability and reproducibility of cement slurries.

Polymers that contribute to reducing fluid loss as described above may be included in fluids. When included in a fluid, the polymer referred to as fluid loss control additives or polymeric fluid loss control additives. A cement slurry may be prepared to include a fluid loss additive. The fluid loss of the cement may be measured with standardized laboratory equipment and techniques to calculate a laboratory fluid loss. In the United States, the American Petroleum Institute (API) publishes API RP Practice 10B-2, *Recommended Practice for Testing Well Cements*, First Edition, July 2005, and later editions, which outline how to calculate the API fluid loss for a cement. Typically, a fluid loss requirement is set by an operator or local jurisdiction and for a cement slurry to be pumped, the cement slurry must exhibit an API fluid loss below the set fluid loss requirement. The current methodology for controlling fluid loss is based on a trial-and-error methodology whereby several cement slurries may be prepared and fluid loss for each tested. The slurry designs may be iterated by changing the composition of each slurry until a slurry that meets all the required physical properties, including fluid loss, is achieved. The iterative design process is inefficient and may lead to a cement slurry with increased complexity and requirement to include a fluid loss control additive among other disadvantages. In the present disclosure, a model-based approach for designing for a fluid loss requirement of a cement slurry is disclosed. The present methods may utilize a model of bulk blending optimization to design for reduced fluid loss such that concentration of fluid loss control additives in the cement slurry may be reduced.

BRIEF DESCRIPTION OF THE DRAWINGS

These drawings illustrate certain aspects of some of the embodiments of the present disclosure and should not be used to limit or define the disclosure.

FIG. 4 is a parity plot of fluid loss for a fluid loss experiment.

DETAILED DESCRIPTION

Figure 1:
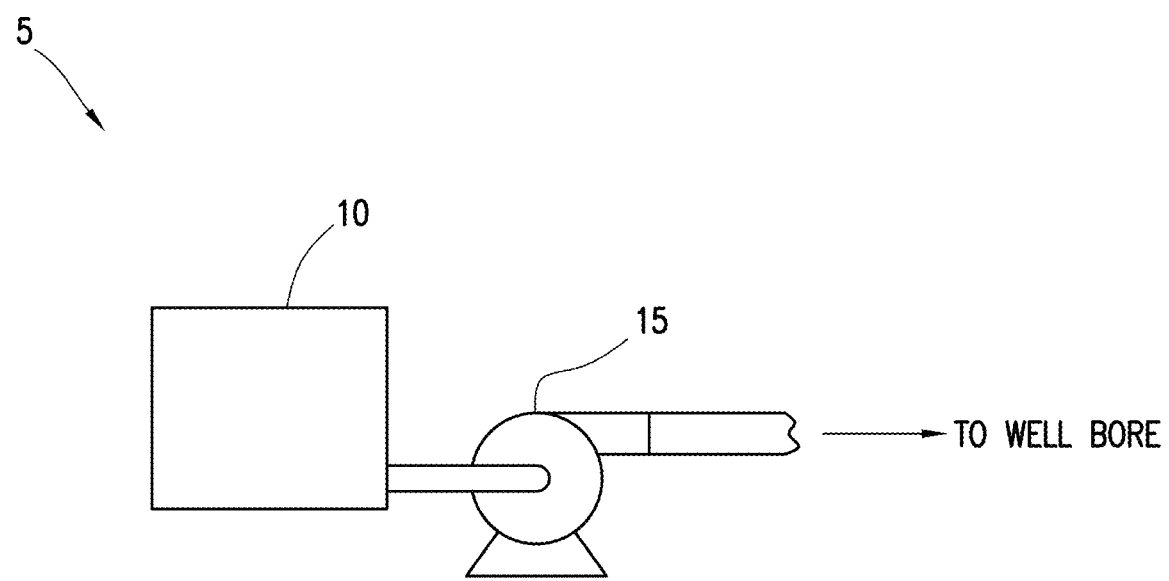
FIG. 1 is a schematic illustration of an example system for the preparation and delivery of a cement slurry to a wellbore.

The present disclosure may generally relate to cementing methods and systems. More particularly, embodiments may be directed to designing cement slurry recipes using a fluid loss model as well as preparing a cement slurry based on the cement slurry recipe.

Cement slurries may include cement, supplementary cementitious additives, inert materials, and chemical additives. Cement slurry recipes, sometimes referred to as a cement design or other equivalent names thereof, may be unique to each well to satisfy the differing design requirements for each well. Cement slurry recipes may be developed such that a cement slurry prepared from the cement slurry recipe meets the design requirements for a cement slurry such as viscosity, density, and rheology, for example, and that a set cement resulting from the setting of the cement slurry meets all the design requirements such as compressive strength, tensile strength, Young's modulus, for example. When the cement slurry recipe is developed, representative samples of cement slurry may be prepared and tested in a laboratory to verify that the cement slurry and set cement have the required physical properties. Fluid loss of a cement slurry prepared from the cement slurry recipe may be measured in a laboratory using standard tests to ensure that the fluid loss remains below a target amount of fluid loss. Once a cement slurry recipe is verified as meeting the design requirements, the cement slurry recipe may be selected for preparation and the prepared slurry may be introduced into a wellbore. A cement slurry for use in cementing wellbores is typically mixed at a wellbore pad site using cement mixing equipment and pumped into the wellbore using cement pumps.

A cement slurry fluid loss model is presented herein. The cement slurry fluid loss model may map cement slurry composition and testing conditions to predict API fluid loss. The cement slurry fluid loss model may be utilized to design a cement slurry recipe to have a target fluid loss. The cement slurry fluid loss model may account for the effect on fluid loss due to bulk blend components such as Portland cement, supplementary cementitious materials, crystalline silica, weighting materials such as beads, and the amount of water. The cement slurry fluid loss model may capture interactions between the bulk components as well as the temperature effects on the contribution of each slurry component to predicted fluid loss.

Fluid loss value of a cement slurry is controlled by several factors including amount of water in the slurry (w), identity of and amount of Portland cement ($P_i$), identity of and amount of cementitious materials ($S_j$), identity of and amount of inert materials ($I_k$), identity of and amount of the chemical additives which may influence the fluid loss ($C_l$), temperature (T), and differential pressure (P). Further, there may be other factors such as sand, salts, and any other kind of additives. A general formula for fluid loss may include equation 1 where f may be a linear or non-linear function and the indices i, j, k, and l represent the possibility of multiple Portland cements, supplementary cementitious materials, inert materials, and chemical additives. In some embodiments, the function f may be described by a neural net, a decision tree, or an explicit mathematical form.

$$FL = f(w, P_i, S_j, I_k, C_l, T, P)$$  Equation 1

One standard for measuring fluid loss is using the procedure set forth in API RP Practice 10B-2 which uses equation 2 to determine fluid loss. In equation 2, FL is fluid loss, V is the volume of fluid collected in mL and t is the time in minutes the fluid loss test is run for. The API test for fluid loss is specified to be carried out for 30 minutes maximum as indicated by the numerator in Equation 2. Equation 2 may be generalized as equation 3 for any arbitrary experiment time length $t_{expt}$.

$$FL = 2 * V * \sqrt{\frac{30}{t}}$$  Equation 2

$$FL = 2 * V * \sqrt{\frac{t_{expt}}{t}}$$  Equation 3

Cement slurries may be prepared by mixing a dry cement blend cement with water. The dry cement blend may be prepared at a bulk cementing plant whereby a cement slurry recipe may be utilized to prepare a dry cement blend. A cement slurry recipe may include a listing of solid and liquid cement components and quantities thereof to include in a bulk dry blend. Cement slurry recipes may be engineered to have a particular fluid loss value such that a cement slurry prepared based on the cement slurry recipe has a predictable value. Typically, the components of the bulk dry blend cement are measured and then dry blended together using appropriate blending machinery. The cement slurry recipe may include listing of bulk materials and amounts thereof to include such as cements which develop compressive strength when mixed with water as well as supplementary cementitious materials which do not develop compressive strength when mixed with water but contribute to compressive strength development when mixed with cement and inert materials which do not contribute to compressive strength development. The cement slurry recipe may further include a listing of chemical additives and amounts thereof such as those chemical additives which modify the physical properties of a cement slurry prepared using the cement slurry recipe or a set cement thereof. Additives may include, but are not limited to, salts, fluid loss control additives, and suspending aids, for example. The cement slurry recipe may further include a listing of amount of water to include when preparing a cement slurry based on the cement slurry recipe. The bulk dry blend cement may be transported to a location, such as a well pad site, where the bulk dry blend cement may be mixed with water, in the quantity listed by the cement slurry recipe or to form a cement slurry with the desired density, which may then be introduced into a wellbore. In some embodiments, the cement slurry recipe may further include liquid additives which may be mixed with the cement slurry.

Oftentimes, the fluid loss value for a slurry is controlled by adjusting a concentration of fluid loss control additive. However, the fluid loss of a cement slurry stems from the choice of the bulk components and amount of water mixed to form the cement slurry. As such, the selection of bulk materials and water may influence the fluid loss observed at a given pressure and temperature. There may be several mechanisms which influence the fluid loss of a bulk material including, but not limited to, packing fraction due to particle shape and size distribution forming a less permeable filter cake. Another fluid loss factor may be bulk materials holding water through sorption mechanisms and gelling of water and bulk materials to form a less permeable layer of filter cake.

Fluid loss may be dependent upon, cement slurry density, temperature, pressure, and concentration of fluid loss control additive, for example. For a simple cement slurry which contains one cementitious material and one fluid loss control additive, a generalized fluid loss model is shown in Equation 4. In equation 4, the function $h(w, P_i)$ captures the fluid loss effect of the amount of water and the amount and specific type of cementitious material, where w is amount of water and $P_i$ is concentration of cementitious material i. This function may be a polynomial, power law, exponential, logarithmic, trigonometric or any transcendental function or an analytic expression, or may even be described by a neural net or a decision tree. In equation 4, the function g( ) captures the effect of a fluid loss control additive. In some examples, the function $g(C_i)$ may be expressed as Equation 5, where $\gamma$ is a measure of effectiveness of the additive to fluid loss control and C is a concentration of fluid loss control additive. Thus, a simple model of fluid loss control may be expressed as equation 6 where w is the amount of water and P is the amount of cementitious material or the sum amount of the cementitious materials ($P_i$) when more than one cementitious material is present. $FL_0$ is a constant which may depend on the specific cementitious material chosen for the cement slurry formulation. The function h(w, P) may depend on the ratio of water and cementitious material and may be a polynomial, power law, exponential, logarithmic, trigonometric or any transcendental function or an analytic expression, or may even be described by a neural net or a decision tree. Some forms of the function h(w, P) may be expressed as Equation 7 and Equation 8. In the following equations, n may be a constant for a given formulation. W is concentration or amount of water.

$$FL = h(w, P) * g(C_i) \qquad \text{Equation 4}$$

$$g(C_i) = \exp(\gamma C) \qquad \text{Equation 5}$$

$$FL = FL_0 h(w, P) * \exp(\gamma C) \qquad \text{Equation 6}$$

$$h(w, P) = \left(\frac{w}{P}\right)^n \qquad \text{Equation 7}$$

$$h(w, P) = \exp\left(n\frac{w}{P}\right) \qquad \text{Equation 8}$$

Equation 4 may be extended for a cement formulation having multiple cementitious materials as in equation 9. In equation 9, $FL_0^i$ is the $FL_0$ value associated with each cementitious material i, P is the amount of cementitious material or the sum amount of the cementitious materials ($P_i$) when more than one cementitious material is present, and $\alpha_i$ is a constant associated with each cementitious material i representative of the effectiveness of a bulk material for controlling fluid loss. Cementitious materials may include any materials included in a dry blend such as cements, supplementary cementitious materials, and inert materials, for example. Equation 9 may be extended to equation 10, where $A_0$ is a constant independent of the slurry composition. $A_0$ may depend on the fluid loss control test set up such as the volume of the fluid loss cell and pressure differential across the cell, for example. Equations 9 and 10 are analytical expressions but may replaced by a polynomial, power law, exponential, logarithmic, trigonometric or any transcendental function or an analytic expression, or may even be described by a neural net or a decision tree or a combination thereof.

$$FL = \left(\sum_i FL_0^i P_i\right) \left(\frac{w}{\sum_k \alpha_i P_i}\right)^n \exp(\gamma C) \qquad \text{Equation 9}$$

$$FL = A_0 * \exp\left(\sum_i FL_0^i P_i\right) \left(\frac{w}{\sum_k \alpha_i P_i}\right)^n \exp(C) \qquad \text{Equation 10}$$

Any of the coefficients in equations 9 and 10 may be a function of temperature and/or pressure. The temperature and pressure dependance itself may be written in various different ways, such as, without limitation, as an Arrhenius expression or a polynomial. The temperature and pressure dependance may also be a power law, logarithmic, trigonometric or any transcendental function or an analytic expression, or may even be described by a neural net or a decision tree or a combination thereof. Equation 11 is the fluid loss for a single bulk component with Arrhenius temperature and pressure dependance where E is the activation energy, $V_0$ is the activation volume, T is the temperature, and $P_r$ is the pressure differential on the fluid loss test set up. The coefficients in any of equation 9, 10 and 11 or in their equivalent counterparts are material coefficient which are related to physico-chemical properties of the material, for example, particle shape, size, size-distribution, morphology, surface charges, dissolvable species, etc. which may determine the value of these material coefficients.

$$FL = FL_0 \exp\left(-\frac{E}{RT}\right) \exp(-V_0 P_r) \left(\frac{w}{P}\right)^n * \exp(\gamma C) \qquad \text{Equation 11}$$

In some examples, there may be interactions between components of the cement slurry. The interactions may enhance effect on fluid loss control resulting in lower net fluid loss when the interacting components are included together in a cement slurry. Alternatively, the fluid loss may be enhanced resulting in greater net fluid loss when interacting components are included in the cement slurry. There may be various reasons for component interactions. For example, the particle size distributions of two interacting materials may be such that the resulting packing of two materials in a filter cake may be much more compact than individual material itself. Without being limited by theory, it is also possible that the particle size and shape of two materials are incompatible for effective packing thus making the filter cake more permeable. Additionally, there may be chemical interactions such release of chemical species which may contribute to chemical reactions which may affect fluid loss. An exemplary fluid loss model which includes interactions between two components is illustrated in equation 12. In equation 12, $P_1$ and $P_2$ are the mass fractions of the two bulk materials, $FL_1$ and $FL_2$ are the fluid loss coefficient related to each bulk material and $FL_{12}$ is the interaction coefficient. Equation 12 may be extended to include any number of components.

$$FL = (FL_1 P_1 + FL_2 P_2 + FL_{12} P_1 P_2) \left(\frac{w}{P}\right)^n * \exp(\gamma C) \qquad \text{Equation 12}$$

As previously discussed, the API procedure set forth in API RP Practice 10B-2 may utilize equation 2 to determine fluid loss. Using the above developed methodology, equation 2 may be extended to develop separate models for volume collected and the time to blowout to obtain the net fluid loss. Equations 13 and 14 illustrate one possibility of the form of equations to describe volume collected and the time to blowout to obtain the net fluid loss. The functional forms k( ) and h( ) may be a linear or non-linear function and may be described by a neural net, decision tress or an explicit mathematical form. In the following equations, $P_i$ is mass fraction of cement component i (such as Portland cement, for example), $S_j$ is mass fraction of supplementary cementitious component j (such as a pozzolan, for example), $I_k$ is mass fraction of inert material k, Cl is mass fraction of chemical additive l, T is temperature, and P is pressure. While expressed as a mass fraction, any equivalent measurement such as volume fraction, molar fraction, or any other measurement may be used. Equation 14 shows time to blow out for 30 minutes as per API recommended practices but may be extended to any desired time. Equations 15 and 16 illustrate one embodiment of equations 13 and 14.

$$V = k(w, P_i, S_j, I_k, C_l, T, P) \qquad \text{Equation 13}$$

$$t = \text{Min}(30, h(w, P_i, S_j, I_k, C_l, T, P)) \qquad \text{Equation 14}$$

$$V = h_v(w, P_i) * g_v(C_i) \qquad \text{Equation 15}$$

$$t = \text{Min}(30, h_t(w, P_i) * g_t(C_i)) \qquad \text{Equation 16}$$

Cement fluid loss control additives may be utilized to reduce fluid loss in a cement slurry. There may be several mechanisms by which a cement fluid loss control additive imparts control over the fluid loss in a slurry. For example, a cement fluid loss control additive may hold additional water by sorption thereby reducing the total volume of water loss or a cement fluid loss control additive may aid in formation of a cement filter cake thereby slowing down the process of fluid loss to formation. It is also possible that the cement fluid loss control additives may form a relatively impermeable layer at the interface of the cement slurry and formation.

A model of fluid loss (FL) for a cement fluid loss control additive for a given cement formulation under specific test conditions may be written as equation 17 where $FL_0$ is the fluid loss without the cement fluid loss control additive and is a function of the blend, amount of water, temperature and pressure test conditions. The function g( ) may be a linear or a non-linear function of the type and amount of the fluid loss control additive. The function may be a polynomial, power law, exponential, logarithmic, trigonometric or any transcendental function or an analytic expression, or may even be described by a neural net or a decision tree. For example, a model of fluid loss for a cement fluid loss control additive may be expressed as equation 18 where coefficients $\beta$ is a measure of the effectiveness of the fluid loss control additive. The value of $\beta$ may be a function of chemical composition, structure, and morphology of the fluid loss control additive. For a polymeric fluid loss control additive, the value of $\beta$ may depend on the molecular weight, radius of gyration, the functional groups on the polymer chain, their location, degree of branching of the chain, electrical charges along the chain and their distribution, and other factors. For latex and latex like materials, the value of $\beta$ may depend on the degree of cross linking, particle size and distribution, shape and surface charges of the particles among other factors. Further, equation 18 may be equivalently expressed as equation 19.

$$FL=FL_0*g(C_i) \qquad \text{Equation 17}$$

$$FL=FL_0*1/(1+\beta C_i) \qquad \text{Equation 18}$$

$$FL=FL_0*\exp(-\beta C_i) \qquad \text{Equation 19}$$

There may be further consideration for effectiveness of a cement fluid loss control additive. For example, there may be a threshold concentration required for a cement fluid loss control additive before it starts to show any effect on the fluid loss value.

$$FL=FL_0*g_T(T,C_i) \qquad \text{Equation 22}$$

$$FL=FL_0*1/(1+\beta(T)C_i) \qquad \text{Equation 23}$$

$$FL=FL_0*\exp(-\beta(T)C_i) \qquad \text{Equation 24}$$

$$FL=FL_0*\exp(-\beta(C_i-C_{0,i})) \qquad \text{Equation 25}$$

In some examples, there may be interactions between cement fluid loss control additives where the interactions may enhance the efficacy or may interfere. Some examples of interactions may include is when a dispersant, salt, suspending aid or a retarder enhance (or reduce) the efficacy of an fluid loss control additive. In some examples the interaction between cement fluid loss control additives may be expressed as equation 26, 26, and 27. In equations 26 and 27, $C_1$ and $C_2$ are the mass fractions of the two cement fluid loss control additives, $\beta_1$ and $\beta_2$ are the fluid loss coefficient related to each cement fluid loss control additive and $\beta_{12}$ is the interaction coefficient. The fluid loss coefficients may be determined experimentally by standard fluid loss tests and utilizing statistical analysis such as analysis of variance. (ANOVA), for example. Equation 27 and 27 may be extended to include any number of components. In some examples, the time to blowout and net fluid loss may be calculated as in equation 29 and 29. These functional forms k( ) and h( ) may be a linear or non-linear function and may be described by a neural net, decision tress or an explicit mathematical form. Equation 30 shows time to blow out for 30 minutes as per API recommended practices but may be extended to any desired time. In some examples, the models for volume and time models may be expressed as equation 31 and 31.

$$FL=FL_0*g_c(C_1,C_2) \qquad \text{Equation 26}$$

$$FL=FL_0*1/(1+\beta_1 C_1+\beta_2 C_2+\beta_{12}C_1 C_2) \qquad \text{Equation 27}$$

$$FL=FL_1*\exp(\beta_1 C_1+\beta_2 C_2+\beta_{12}C_1 C_2) \qquad \text{Equation 28}$$

$$V=k(w,P_t,S_j,I_k,C_l,T,P) \qquad \text{Equation 29}$$

$$t=\text{Min}(30,h(w,P_t,S_j,I_k,C_l,T,P)) \qquad \text{Equation 30}$$

$$V=V_0*g_v(C_i) \qquad \text{Equation 31}$$

$$t=\text{Min}(30,t_0*g_t(C_i)) \qquad \text{Equation 32}$$

FIG. 1 illustrates an example system 5 for preparation of a cement slurry including and delivery of the cement slurry to a wellbore. The cement slurry may be any cement slurry disclosed herein. A cement slurry recipe be developed, for example, using the cement fluid loss models described herein, and a cement slurry may be prepared based on the cement slurry recipe. As shown, the cement slurry may be mixed in mixing equipment 10, such as a jet mixer, re-circulating mixer, or a batch mixer, for example, and then pumped via pumping equipment 15 to the wellbore. In some examples, the mixing equipment 10 and the pumping equipment 15 may be disposed on one or more cement trucks as will be apparent to those of ordinary skill in the art. In some examples, a jet mixer may be used, for example, to continuously mix a dry blend including the cement slurry, for example, with the water as it is being pumped to the wellbore.

Figure 2:
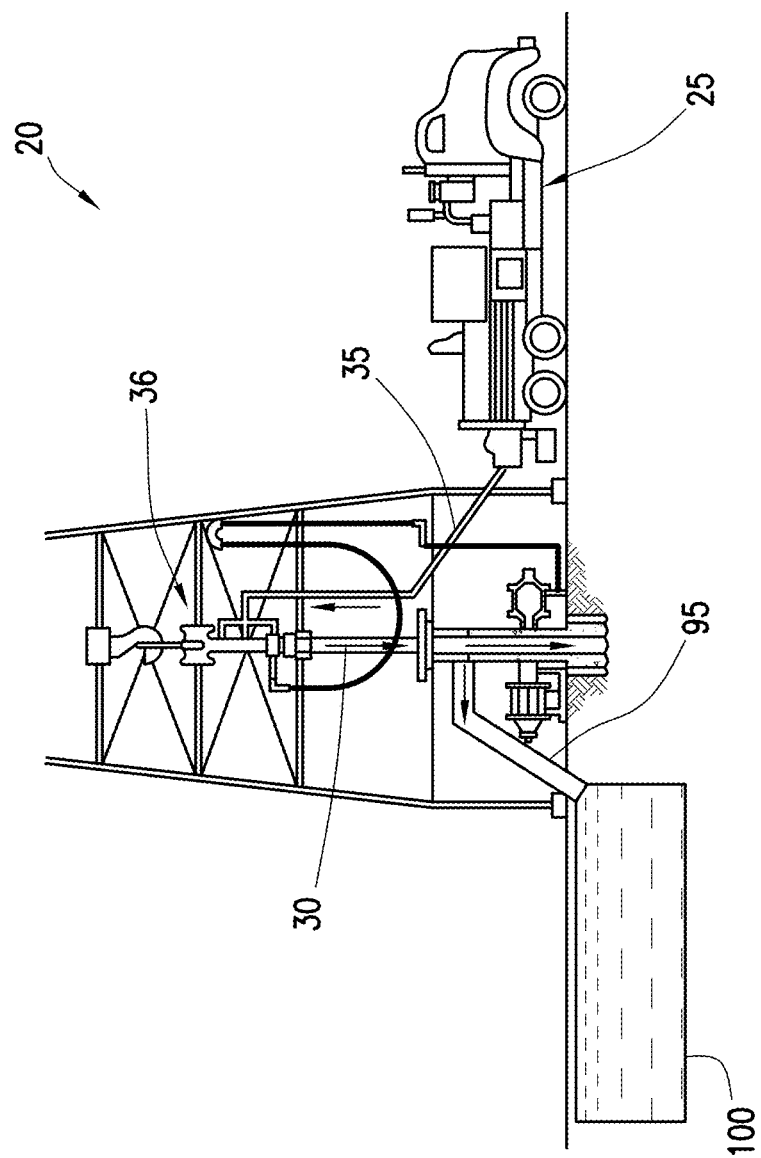
FIG. 2 is a schematic illustration of example surface equipment that may be used in the placement of a cement slurry in a wellbore.

An example technique for placing a cement slurry into a subterranean formation will now be described with reference to FIGS. 2 and 3. FIG. 2 illustrates example surface equipment 20 that may be used in placement of a cement slurry. The cement slurry may be any cement slurry disclosed herein. A cement slurry recipe be developed, for example, using the cement fluid loss models described herein, and a cement slurry may be prepared based on the cement slurry recipe. It should be noted that while FIG. 2 generally depicts a land-based operation, those skilled in the art will readily recognize that the principles described herein are equally applicable to subsea operations that employ floating or sea-based platforms and rigs, without departing from the scope of the disclosure. As illustrated by FIG. 2, the surface equipment 20 may include a cementing unit 25, which may include one or more cement trucks. The cementing unit 25 may include mixing equipment 10 and pumping equipment 15 (e.g., FIG. 1) as will be apparent to those of ordinary skill in the art. The cementing unit 25 may pump a cement slurry 30 through a feed pipe 35 and to a cementing head 36 which conveys the cement slurry 30 downhole.

Figure 3:
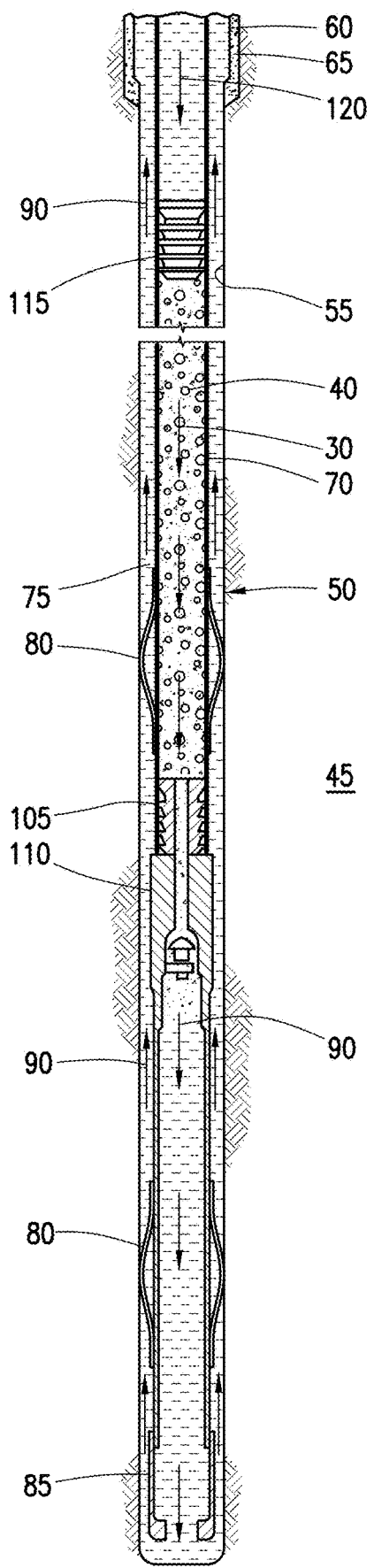
FIG. 3 is a schematic illustration of the example placement of a cement slurry into a wellbore annulus.

Turning now to FIG. 3, the cement slurry 30, may be placed into a subterranean formation 45. As illustrated, a wellbore 50 may be drilled into one or more subterranean formations 45. While the wellbore 50 is shown extending generally vertically into the one or more subterranean formation 45, the principles described herein are also applicable to wellbores that extend at an angle through the one or more subterranean formations 45, such as horizontal and slanted wellbores. As illustrated, the wellbore 50 includes walls 55. In the illustrated example, a surface casing 60 has been inserted into the wellbore 50. The surface casing 60 may be cemented to the walls 55 of the wellbore 50 by cement sheath 65. In the illustrated example, one or more additional conduits (e.g., intermediate casing, production casing, liners, etc.), shown here as casing 70 may also be disposed in the wellbore 50. As illustrated, there is a wellbore annulus 75 formed between the casing 70 and the walls 55 of the wellbore 50 and/or the surface casing 60. One or more centralizers 80 may be attached to the casing 70, for example, to centralize the casing 70 in the wellbore 50 prior to and during the cementing operation.

With continued reference to FIG. 3, the cement slurry 30 may be pumped down the interior of the casing 70. The cement slurry 30 may be allowed to flow down the interior of the casing 70 through the casing shoe 85 at the bottom of the casing 70 and up around the casing 70 into the wellbore annulus 75. The cement slurry 30 may be allowed to set in the wellbore annulus 75, for example, to form a cement sheath that supports and positions the casing 70 in the wellbore 50. While not illustrated, other techniques may also be utilized for introduction of the cement slurry 30. By way of example, reverse circulation techniques may be used that include introducing the cement slurry 30 into the subterranean formation 45 by way of the wellbore annulus 75 instead of through the casing 70.

As it is introduced, the cement slurry 30 may displace other fluids 90, such as drilling fluids and/or spacer fluids that may be present in the interior of the casing 70 and/or the wellbore annulus 75. At least a portion of the displaced fluids 90 may exit the wellbore annulus 75 via a flow line 95 and be deposited, for example, in one or more retention pits 100 (e.g., a mud pit), as shown on FIG. 2. Referring again to FIG. 3, a bottom plug 105 may be introduced into the wellbore 50 ahead of the cement slurry 30, for example, to separate the cement slurry 30 from the other fluids 90 that may be inside the casing 70 prior to cementing. After the bottom plug 105 reaches the landing collar 110, a diaphragm or other suitable device should rupture to allow the cement slurry 30 through the bottom plug 105. In FIG. 3, the bottom plug 105 is shown on the landing collar 110. In the illustrated example, a top plug 115 may be introduced into the wellbore 50 behind the cement slurry 30. The top plug 115 may separate the cement slurry 30 from a displacement fluid 120 and push the cement slurry 30 through the bottom plug 105.

Figure 4:
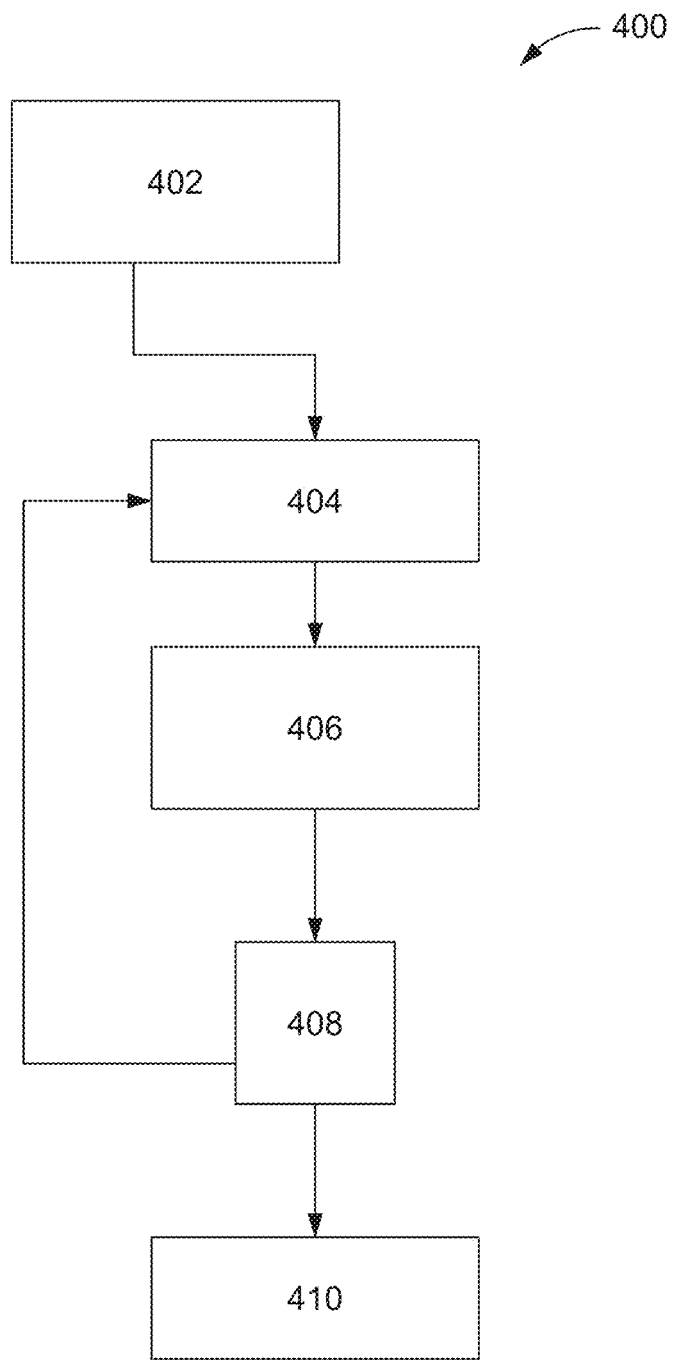
FIG. 4 is a flow chart illustrating a method to design for fluid loss.

FIG. 4 is a flow chart for a method 400 for preparing a cement slurry recipe. Method 400 may begin at step 402 where bulk material availability such as cement, supplementary cementitious materials, and cement additives available may be defined. Bulk material availability is typically location dependent whereby some geographic locations may have access to bulk materials that other geographic locations do not. In step 402, engineering parameters such as fluid loss control requirements may be defined as well as compressive strength requirement, rheology requirement, and density requirement, for example. Other engineering parameters may include, but are not limited to, constraints on the composition of the bulk blend such as inclusion or exclusion of a component, that the slurry must be mixable, must meet a certain thickening time, must satisfy a strength development profile, meet transition time, meet shrinkage/expansion targets, mechanical properties such as tensile strength, elasticity, and permeability.

After defining materials available and engineering parameters, method 400 may proceed to step 404. In step 404, a first proposed cement slurry recipe may be selected which may include cement components and mass fractions thereof, water and mass fraction thereof. Method 400 may proceed to step 406 whereby any of the models of cement fluid loss developed above may be utilized to calculate a predicted fluid loss for the first proposed cement slurry recipe. From step 406, method 400 may proceed to step 408 whereby the calculated fluid loss from step 406 may be compared against the fluid loss defined in step 402. If predicted fluid loss from step 406 is less than the fluid loss defined in step 402, the method may proceed to step 410 where a slurry may be prepared based on the first proposed cement slurry recipe and tested using laboratory techniques to measure the fluid loss to verify the cement slurry meets the fluid loss control requirement in step 402. If the calculated fluid loss from step 406 does not meet the fluid loss defined in step 402, the method may proceed back to step 404 where a second proposed cement slurry recipe may be selected may be selected which may include disparate cement components and/or disparate mass fractions thereof and or chemical additives and components thereof. A predicted fluid loss of the second proposed cement slurry recipe may be calculated in step 406 and compared to the fluid loss control requirement from step 402. If predicted fluid loss from step 406 is less than the fluid loss defined in step 402, the method may proceed to step 410 where a slurry may be prepared based on the first proposed cement slurry recipe and tested using laboratory techniques to measure the fluid loss to verify the cement slurry meets the fluid loss control requirement in step 402. Otherwise, the method may be repeated until a cement slurry recipe that meets or stays below the fluid loss control requirement is met.

Cement slurries described herein may generally include a hydraulic cement and water. A variety of hydraulic cements may be utilized in accordance with the present disclosure, including, but not limited to, those comprising calcium, aluminum, silicon, oxygen, iron, and/or sulfur, which set and harden by reaction with water. Suitable hydraulic cements may include, but are not limited to, Portland cements, pozzolana cements, gypsum cements, high alumina content cements, silica cements, and any combination thereof. In certain examples, the hydraulic cement may include a Portland cement. In some examples, the Portland cements may include Portland cements that are classified as Classes A, C, H, and G cements according to American Petroleum Institute, *API Specification for Materials and Testing for Well Cements*, API Specification 10, Fifth Ed., Jul. 1, 1990. In addition, hydraulic cements may include cements classified by American Society for Testing and Materials (ASTM) in C150 (Standard Specification for Portland Cement), C595 (Standard Specification for Blended Hydraulic Cement) or C1157 (Performance Specification for Hydraulic Cements) such as those cements classified as ASTM Type I, II, or III. The hydraulic cement may be included in the cement slurry in any amount suitable for a particular composition. Without limitation, the hydraulic cement may be included in the cement slurries in an amount in the range of from about 10% to about 80% by weight of dry blend in the cement slurry. For example, the hydraulic cement may be present in an amount ranging between any of and/or including any of about 10%, about 15%, about 20%, about 25%, about 30%, about 35%, about 40%, about 45%, about 50%, about 55%, about 60%, about 65%, about 70%, about 75%, or about 80% by weight of the cement slurries.

The water may be from any source provided that it does not contain an excess of compounds that may undesirably affect other components in the cement slurries. For example, a cement slurry may include fresh water or saltwater. Saltwater generally may include one or more dissolved salts therein and may be saturated or unsaturated as desired for a particular application. Seawater or brines may be suitable for use in some examples. Further, the water may be present in an amount sufficient to form a pumpable slurry. In certain examples, the water may be present in the cement slurry in an amount in the range of from about 33% to about 200% by weight of the cementitious materials. For example, the water cement may be present in an amount ranging between any of and/or including any of about 33%, about 50%, about 75%, about 100%, about 125%, about 150%, about 175%, or about 200% by weight of the cementitious materials. The cementitious materials referenced may include all components which contribute to the compressive strength of the cement slurry such as the hydraulic cement and supplementary cementitious materials, for example.

As mentioned above, the cement slurry may include supplementary cementitious materials. The supplementary cementitious material may be any material that contributes to the desired properties of the cement slurry. Some supplementary cementitious materials may include, without limitation, fly ash, blast furnace slag, silica fume, pozzolans, kiln dust, and clays, for example.

The cement slurry may include kiln dust as a supplementary cementitious material.

"Kiln dust," as that term is used herein, refers to a solid material generated as a by-product of the heating of certain materials in kilns. The term "kiln dust" as used herein is intended to include kiln dust made as described herein and equivalent forms of kiln dust. Depending on its source, kiln dust may exhibit cementitious properties in that it can set and harden in the presence of water. Examples of suitable kiln dusts include cement kiln dust, lime kiln dust, and combinations thereof. Cement kiln dust may be generated as a by-product of cement production that is removed from the gas stream and collected, for example, in a dust collector. Usually, large quantities of cement kiln dust are collected in the production of cement that are commonly disposed of as waste. The chemical analysis of the cement kiln dust from various cement manufactures varies depending on a number of factors, including the particular kiln feed, the efficiencies of the cement production operation, and the associated dust collection systems. Cement kiln dust generally may include a variety of oxides, such as $SiO_2$, $Al_2O_3$, $Fe_2O_3$, CaO, MgO, $SO_3$, $Na_2O$, and $K_2O$. The chemical analysis of lime kiln dust from various lime manufacturers varies depending on several factors, including the particular limestone or dolomitic limestone feed, the type of kiln, the mode of operation of the kiln, the efficiencies of the lime production operation, and the associated dust collection systems. Lime kiln dust generally may include varying amounts of free lime and free magnesium, lime stone, and/or dolomitic limestone and a variety of oxides, such as $SiO_2$, $Al_2O_3$, $Fe_2O_3$, CaO, MgO, $SO_3$, $Na_2O$, and $K_2O$, and other components, such as chlorides. A cement kiln dust may be added to the cement slurry prior to, concurrently with, or after activation. Cement kiln dust may include a partially calcined kiln feed which is removed from the gas stream and collected in a dust collector during the manufacture of cement. The chemical analysis of CKD from various cement manufactures varies depending on a number of factors, including the particular kiln feed, the efficiencies of the cement production operation, and the associated dust collection systems. CKD generally may comprise a variety of oxides, such as $SiO_2$, $Al_2O_3$, $Fe_2O_3$, CaO, MgO, $SO_3$, $Na_2O$, and $K_2O$. The CKD and/or lime kiln dust may be included in examples of the cement slurry in an amount suitable for a particular application.

In some examples, the cement slurry may further include one or more of slag, natural glass, shale, amorphous silica, or metakaolin as a supplementary cementitious material. Slag is generally a granulated, blast furnace by-product from the production of cast iron including the oxidized impurities found in iron ore. The cement may further include shale. A variety of shales may be suitable, including those including silicon, aluminum, calcium, and/or magnesium. Examples of suitable shales include vitrified shale and/or calcined shale. In some examples, the cement slurry may further include amorphous silica as a supplementary cementitious material. Amorphous silica is a powder that may be included in embodiments to increase cement compressive strength. Amorphous silica is generally a byproduct of a ferrosilicon production process, wherein the amorphous silica may be formed by oxidation and condensation of gaseous silicon suboxide, SiO, which is formed as an intermediate during the process In some examples, the cement slurry may further include a variety of fly ashes as a supplementary cementitious material which may include fly ash classified as Class C, Class F, or Class N fly ash according to American Petroleum Institute, API Specification for Materials and Testing for Well Cements, API Specification 10, Fifth Ed., Jul. 1, 1990. In some examples, the cement slurry may further include zeolites as supplementary cementitious materials. Zeolites are generally porous alumino-silicate minerals that may be either natural or synthetic. Synthetic zeolites are based on the same type of structural cell as natural zeolites and may comprise aluminosilicate hydrates. As used herein, the term "zeolite" refers to all natural and synthetic forms of zeolite.

Where used, one or more of the aforementioned supplementary cementitious materials may be present in the cement slurry. For example, without limitation, one or more supplementary cementitious materials may be present in an amount of about 0.1% to about 80% by weight of the cement slurry. For example, the supplementary cementitious materials may be present in an amount ranging between any of and/or including any of about 0.1%, about 10%, about 20%, about 30%, about 40%, about 50%, about 60%, about 70%, or about 80% by weight of the cement.

In some examples, the cement slurry may further include hydrated lime. As used herein, the term "hydrated lime" will be understood to mean calcium hydroxide. In some embodiments, the hydrated lime may be provided as quicklime (calcium oxide) which hydrates when mixed with water to form the hydrated lime. The hydrated lime may be included in examples of the cement slurry, for example, to form a hydraulic composition with the supplementary cementitious components. For example, the hydrated lime may be included in a supplementary cementitious material-to-hydrated-lime weight ratio of about 10:1 to about 1:1 or 3:1 to about 5:1. Where present, the hydrated lime may be included in the set cement slurry in an amount in the range of from about 10% to about 100% by weight of the cement slurry, for example. In some examples, the hydrated lime may be present in an amount ranging between any of and/or including any of about 10%, about 20%, about 40%, about 60%, about 80%, or about 100% by weight of the cement slurry. In some examples, the cementitious components present in the cement slurry may consist essentially of one or more supplementary cementitious materials and the hydrated lime. For example, the cementitious components may primarily comprise the supplementary cementitious materials and the hydrated lime without any additional components (e.g., Portland cement, fly ash, slag cement) that hydraulically set in the presence of water.

Lime may be present in the cement slurry in several; forms, including as calcium oxide and or calcium hydroxide or as a reaction product such as when Portland cement reacts with water. Alternatively, lime may be included in the cement slurry by amount of silica in the cement slurry. A cement slurry may be designed to have a target lime to silica weight ratio. The target lime to silica ratio may be a molar ratio, molal ratio, or any other equivalent way of expressing a relative amount of silica to lime. Any suitable target time to silica weight ratio may be selected including from about 10/90 lime to silica by weight to about 40/60 lime to silica by weight. Alternatively, about 10/90 lime to silica by weight to about 20/80 lime to silica by weight, about 20/80 lime to silica by weight to about 30/70 lime to silica by weight, or about 30/70 lime to silica by weight to about 40/63 lime to silica by weight.

Other additives suitable for use in subterranean cementing operations also may be included in embodiments of the cement slurry. Examples of such additives include, but are not limited to: weighting agents, lightweight additives, gas-generating additives, mechanical-property-enhancing additives, lost-circulation materials, filtration-control additives, fluid-loss-control additives, defoaming agents, foaming agents, thixotropic additives, and combinations thereof. In embodiments, one or more of these additives may be added to the cement slurry after storing but prior to the placement of a cement slurry into a subterranean formation. In some examples, the cement slurry may further include a dispersant. Examples of suitable dispersants include, without limitation, sulfonated-formaldehyde-based dispersants (e.g., sulfonated acetone formaldehyde condensate) or polycarboxylated ether dispersants. In some examples, the dispersant may be included in the cement slurry in an amount in the range of from about 0.01% to about 5% by weight of the cementitious materials. In specific examples, the dispersant may be present in an amount ranging between any of and/or including any of about 0.01%, about 0.1%, about 0.5%, about 1%, about 2%, about 3%, about 4%, or about 5% by weight of the cementitious materials.

In some examples, the cement slurry may further include a set retarder. A broad variety of set retarders may be suitable for use in the cement slurries. For example, the set retarder may comprise phosphonic acids, such as ethylenediamine tetra(methylene phosphonic acid), diethylenetriamine penta (methylene phosphonic acid), etc.; lignosulfonates, such as sodium lignosulfonate, calcium lignosulfonate, etc.; salts such as stannous sulfate, lead acetate, monobasic calcium phosphate, organic acids, such as citric acid, tartaric acid, etc.; cellulose derivatives such as hydroxyl ethyl cellulose (HEC) and carboxymethyl hydroxyethyl cellulose (CMHEC); synthetic co- or ter-polymers comprising sulfonate and carboxylic acid groups such as sulfonate-functionalized acrylamide-acrylic acid co-polymers; borate compounds such as alkali borates, sodium metaborate, sodium tetraborate, potassium pentaborate; derivatives thereof, or mixtures thereof. Examples of suitable set retarders include, among others, phosphonic acid derivatives. Generally, the set retarder may be present in the cement slurry in an amount sufficient to delay the setting for a desired time. In some examples, the set retarder may be present in the cement slurry in an amount in the range of from about 0.01% to about 10% by weight of the cementitious materials. In specific examples, the set retarder may be present in an amount ranging between any of and/or including any of about 0.01%, about 0.1%, about 1%, about 2%, about 4%, about 6%, about 8%, or about 10% by weight of the cementitious materials.

In some examples, the cement slurry may further include an accelerator. A broad variety of accelerators may be suitable for use in the cement slurries. For example, the accelerator may include, but are not limited to, aluminum sulfate, alums, calcium chloride, calcium nitrate, calcium nitrite, calcium formate, calcium sulphoaluminate, calcium sulfate, gypsum-hemihydrate, sodium aluminate, sodium carbonate, sodium chloride, sodium silicate, sodium sulfate, ferric chloride, or a combination thereof. In some examples, the accelerators may be present in the cement slurry in an amount in the range of from about 0.01% to about 10% by weight of the cementitious materials. In specific examples, the accelerators may be present in an amount ranging between any of and/or including any of about 0.01%, about 0.1%, about 1%, about 2%, about 4%, about 6%, about 8%, or about 10% by weight of the cementitious materials.

Cement slurries generally should have a density suitable for a particular application. By way of example, the cement slurry may have a density in the range of from about 8 pounds per gallon ("ppg") (959 kg/m$^3$) to about 20 ppg (2397 kg/m$^3$), or about 8 ppg to about 12 ppg (1437. kg/m$^3$), or about 12 ppg to about 16 ppg (1917.22 kg/m$^3$), or about 16 ppg to about 20 ppg, or any ranges therebetween. Examples of the cement slurry may be foamed or unfoamed or may comprise other means to reduce their densities, such as hollow microspheres, low-density elastic beads, or other density-reducing additives known in the art.

The cement slurries disclosed herein may be used in a variety of subterranean applications, including primary and remedial cementing. The cement slurries may be introduced into a subterranean formation and allowed to set. In primary cementing applications, for example, the cement slurries may be introduced into the annular space between a conduit located in a wellbore and the walls of the wellbore (and/or a larger conduit in the wellbore), wherein the wellbore penetrates the subterranean formation. The cement slurry may be allowed to set in the annular space to form an annular sheath of hardened cement. The cement slurry may form a barrier that prevents the migration of fluids in the wellbore. The cement slurry may also, for example, support the conduit in the wellbore. In remedial cementing applications, the cement slurry may be used, for example, in squeeze cementing operations or in the placement of cement plugs. By way of example, the cement slurry may be placed in a wellbore to plug an opening (e.g., a void or crack) in the formation, in a gravel pack, in the conduit, in the cement sheath, and/or between the cement sheath and the conduit (e.g., a micro annulus).

The following statements may describe certain embodiments of the disclosure but should be read to be limiting to any particular embodiment.

Statement 1. A method of designing a cement slurry comprising: (a) selecting at least a cementitious material and concentration thereof, a water and concentration thereof, and a fluid loss control additive and concentration thereof to form a cement slurry recipe; (b) calculating a fluid loss of the cement slurry recipe using a fluid loss model; (c) comparing the fluid loss of the cement slurry recipe to a fluid loss requirement, wherein steps (a)-(c) are repeated if the fluid loss of the cement slurry recipe does not meet or stay below the fluid loss requirement, wherein each repeated step of selecting comprises selecting different concentrations and/or different chemical identities for the one or more chemical additives, cementitious material, or water than previously selected, or step (d) is performed if the fluid loss of the cement slurry recipe meets or stays below the fluid loss requirement; and (d) preparing a cement slurry based on the cement slurry recipe.

Statement 2. The method of statement 1 wherein the cement slurry recipe further comprises one or more chemical additives is selected from the group consisting of weighting agents, lightweight additives, gas-generating additives, mechanical-property-enhancing additives, lost-circulation control materials, filtration-control additives, defoaming agents, foaming agents, thixotropic additives, dispersants, suspending aids, viscosifiers, transition time control additives and combinations thereof.

Statement 3. The method of statements 1 or 2 wherein the one or more chemical additives is a cement fluid loss control additive.

Statement 4. The method of any of statements 1-3 wherein the fluid loss model comprises an equation of the following form: $FL=FL_0 h(w,P_i)*\exp(\gamma C)$ where FL is fluid loss, $FL_0$ is a constant, $\gamma$ is a measure of effectiveness of fluid loss control additive, C is a concentration of fluid loss control additive, $h()$ is a function, w amount of water and $P_i$ is concentration of cementitious material i.

Statement 5. The method of any of statements 1-4 wherein $h()$ is at least one of a polynomial function, power law function, exponential function, logarithmic function, trigonometric function, transcendental function, analytic expression, a neural net, a decision tree, or a combination thereof.

Statement 6. The method of any of statements 1-5 wherein the fluid loss model comprises an equation of the following form:

$$FL = \left(\sum_i FL_0^i P_i\right)\left(\frac{w}{\sum_i \alpha_i P_i}\right)^n \exp(\gamma C)$$

where FL is fluid loss, $FL_0^i$ is a constant for each cementitious material i in the cement slurry, $P_i$ is concentration of cementitious material i, w is amount of water, $\alpha_i$ is a constant, $\gamma$ is a measure of effectiveness of fluid loss control additive, n is a constant, and C is a concentration of fluid loss control additive.

Statement 7. The method of any of statements 1-5 wherein the fluid loss model comprises an equation of the following form:

$$FL = FL_0 \exp\left(-\frac{E}{RT}\right)\exp(-V_0 P_r)\left(\frac{w}{P}\right)*\exp(\gamma C)$$

where FL is fluid loss $FL_0$ is a constant, $\gamma$ is a measure of effectiveness of fluid loss control additive, C is a concentration of fluid loss control additive, E is activation energy, $V_0$ is activation volume, T is temperature, $P_r$ is pressure differential, R is universal gas constant, w is amount of water, and P is the amount of cementitious material or the sum amount of the cementitious materials ($P_i$) when more than one cementitious material is present.

Statement 8. The method of any of statements 1-5 wherein the fluid loss model comprises an equation of the following form:

$$FL = (FL_1 P_1 + FL_2 P_2 + FL_{12} P_1 P_2)\left(\frac{w}{P}\right)*\exp(\gamma C)$$

where FL is fluid loss, $FL_1$ and $FL_2$ are fluid loss coefficients for cement and chemical additive, $P_1$ and $P_2$ are concentrations of cement and chemical additive, $FL_{12}$ is an interaction coefficient, w is amount of water, P is the amount of cementitious material or the sum amount of the cementitious materials ($P_i$) when more than one cementitious material is present, $\gamma$ is a measure of effectiveness of fluid loss control additive, and C is a concentration of fluid loss control additive.

Statement 9. The method of any of statements 1-5 wherein the fluid loss model comprises an equation of the following form: $FL=FL_0*g(C_i)$ where FL is fluid loss $FL_0$ is a constant $C_i$ is concentration of fluid loss control additive and $g(\ )$ is at least one of a polynomial function, power law function, exponential function, logarithmic function, trigonometric function, transcendental function, analytic expression, a neural net, a decision tree, or a combination thereof.

Statement 10. The method of any of statements 1-5 wherein the fluid loss model comprises an equation of the following form: $FL=FL_0*1/(1+\beta C_i)$ where FL is fluid loss $FL_0$ is a constant $C_i$ is concentration of fluid loss control additive, and $\beta$ is a constant associated with physicochemical properties of the fluid loss control additive.

Statement 11. The method of any of statements 1-5 wherein the fluid loss model comprises an equation of the following form: $FL=FL_0*\exp(-\beta C_i)$ where FL is fluid loss $FL_0$ is a constant $C_i$ is concentration of fluid loss control additive, and $\beta$ is a constant associated with physicochemical properties of the fluid loss control additive.

Statement 12. The method of any of statements 1-11 further comprising placing the cement slurry in a subterranean formation.

Statement 13. A method comprising: (a) providing a fluid loss model; (b) providing a fluid loss requirement; (c) generating a cement slurry recipe using the fluid loss model and the fluid loss requirement such that a calculated fluid loss of the cement slurry recipe using the fluid loss model meets or exceeds the fluid loss requirement; and (d) preparing a cement slurry based on the cement slurry recipe.

Statement 14. The method of statement 13 wherein the fluid loss model comprises an equation of the following form:

$$FL = \left(\sum_i FL_0^i P_i\right)\left(\frac{w}{\sum_i \alpha_i P_i}\right)^n \exp(\gamma C)$$

where FL is fluid loss, $FL_0^i$ is a constant for each cementitious material i in the cement slurry, $P_i$ is concentration of cementitious material i, w is amount of water, $\alpha_i$ is a constant, $\gamma$ is a measure of effectiveness of fluid loss control additive, and C is a concentration of fluid loss control additive.

Statement 15. The method of statement 13 wherein the fluid loss model comprises an equation of the following form:

$$FL = FL_0 \exp\left(-\frac{E}{RT}\right)\exp(-V_0 P_r)\left(\frac{w}{P}\right)^n *\exp(\gamma C)$$

where FL is fluid loss $FL_0$ is a constant, $\gamma$ is a measure of effectiveness of fluid loss control additive, C is a concentration of fluid loss control additive, E is activation energy, $V_0$ is activation volume, T is temperature, $P_r$ is pressure differential, R is universal gas constant, w is amount of water, and P is the amount of cementitious material or the sum amount of the cementitious materials ($P_i$) when more than one cementitious material is present.

Statement 16. The method of statement 13 wherein the fluid loss model comprises an equation of the following form:

$$FL = (FL_1 P_1 + FL_2 P_2 + FL_{12} P_1 P_2)\left(\frac{w}{P}\right) * \exp(\gamma C)$$

where FL is fluid loss, $FL_1$ and $FL_2$ are fluid loss coefficients for cement and chemical additive, $P_1$ and $P_2$ are concentrations of cement and chemical additive, $FL_{12}$ is an interaction coefficient, w is amount of water, P is the amount of cementitious material or the sum amount of the cementitious materials ($P_i$) when more than one cementitious material is present, $\gamma$ is a measure of effectiveness of fluid loss control additive, and C is a concentration of fluid loss control additive.

Statement 17. The method of statement 13 wherein the fluid loss model comprises an equation of the following form: $FL=FL_0*g(C_i)$ where FL is fluid loss $FL_0$ is a constant $C_i$ is concentration of fluid loss control additive and g( ) is at least one of a polynomial function, power law function, exponential function, logarithmic function, trigonometric function, transcendental function, analytic expression, a neural net, a decision tree, or a combination thereof.

Statement 18. The method of statement 13 wherein the fluid loss model comprises an equation of the following form: $FL=FL_0*1/(1+\beta C_i)$ where FL is fluid loss $FL_0$ is a constant $C_i$ is concentration of fluid loss control additive, and $\beta$ is a constant associated with physico-chemical properties of the fluid loss control additive.

Statement 19. The method of statement 13 wherein the fluid loss model comprises an equation of the following form: $FL=FL_0*\exp(-\beta C_i)$ where FL is fluid loss $FL_0$ is a constant $C_i$ is concentration of fluid loss control additive, and $\beta$ is a constant associated with physico-chemical properties of the fluid loss control additive.

Statement 20. The method of any of statements 13 further comprising introducing the cement slurry in a subterranean formation.

EXAMPLES

To facilitate a better understanding of the present disclosure, the following examples of certain aspects of some embodiments are given. In no way should the following examples be read to limit, or define, the entire scope of the disclosure.

Example 1

Figure 5:
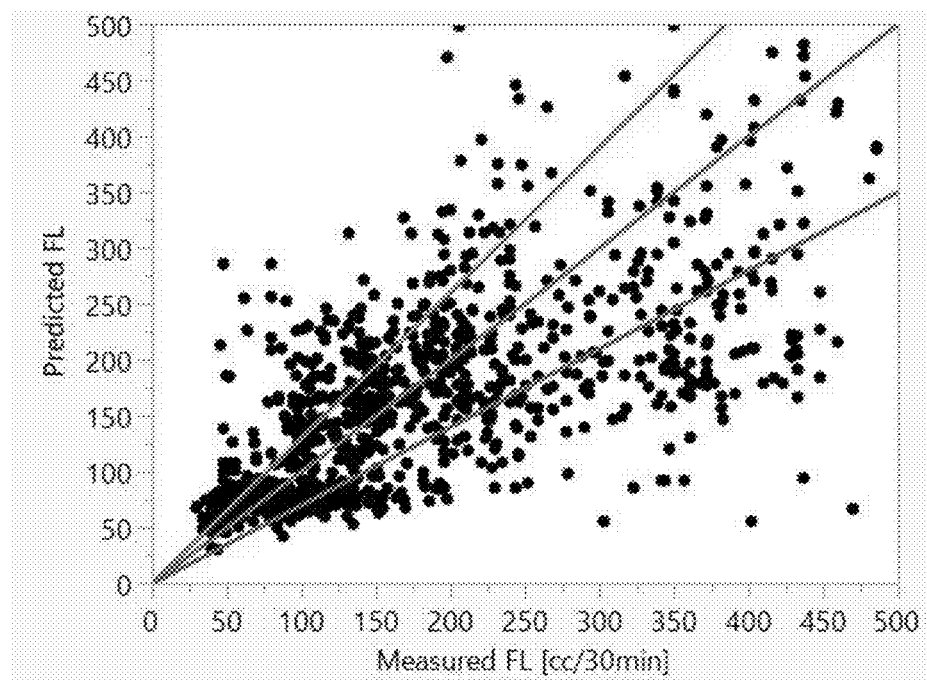
FIG. 5 is a parity plot of fluid loss for a fluid loss experiment.

A series of static fluid loss tests were performed according to API RP Practice 10B-2 for various bulk materials including different types and amounts of Portland cement, fly Ash, cement kiln dust, slag, volcanic ash, crystalline silica, silica fume, various heavyweight and lightweight materials. Additionally, various fluid loss control materials, dispersants, suspending aids, retarders, salt, and expansion aids were included in various amounts. In the data set, the slurry density varied from low of 9 ppg (1078.4 kg/m$^3$) to high of 20 ppg (2396.5 kg/m$^3$) and the temperature ranged from 80° F. (26.6° C.) to 200° F. (93.3° C.). Slurries were prepared and tested according to API RP Practice 10B-2 and the fluid loss for each slurry was determined. The observed slurry fluid loss was compared to a predicted slurry fluid loss from the equations previously presented. A parity plot was created from the observed fluid loss to predicted fluid loss and is shown in FIG. 5. It can be observed from the results of the fluid loss tests that the aforementioned modeling approach can successfully describe the fluid loss behavior of a different types of bulk material across a wide range of temperature and water conditions.

Example 2

Figure 6:
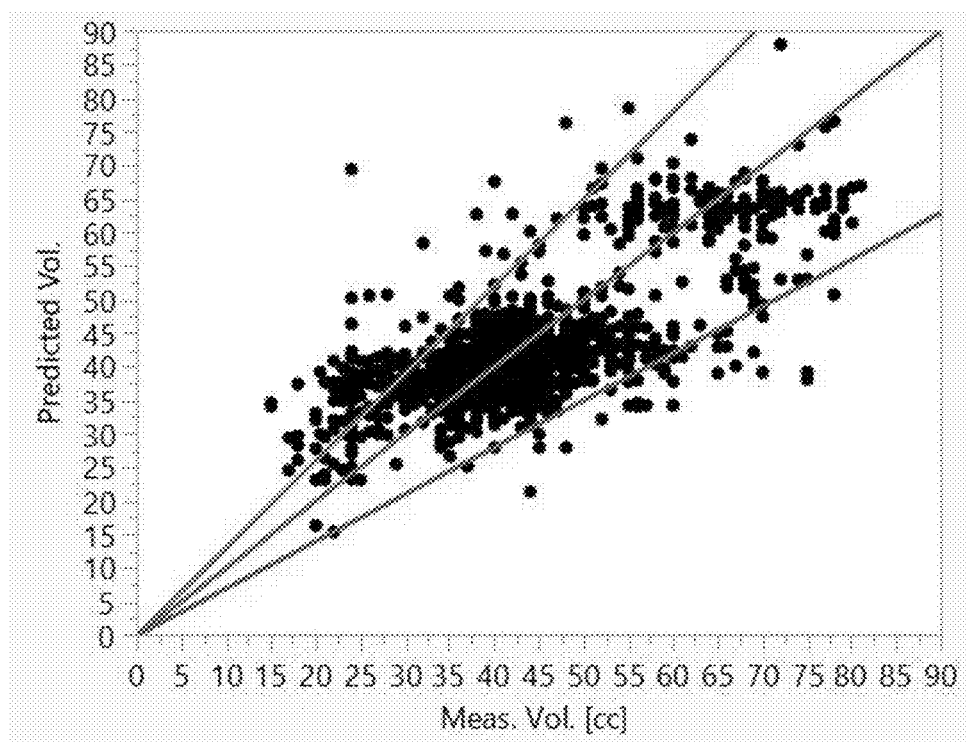
FIG. 6 is a parity plot of fluid loss for a fluid loss experiment.

The data from Example 1 was used in conjunction with equations 13-16 to estimate the volume of fluid collected in the experiment. The model predictions of volume collected in the experiment were compared with the actual volume collected in the experiment. A parity plot was created from the observed fluid loss to predicted fluid loss and is shown in FIG. 6. It can be observed from FIG. 6 that the model predictions of volume collected can successfully describe the fluid loss behavior of a different types of bulk material across a wide range of temperature and water conditions.

Example 3

Figure 7:
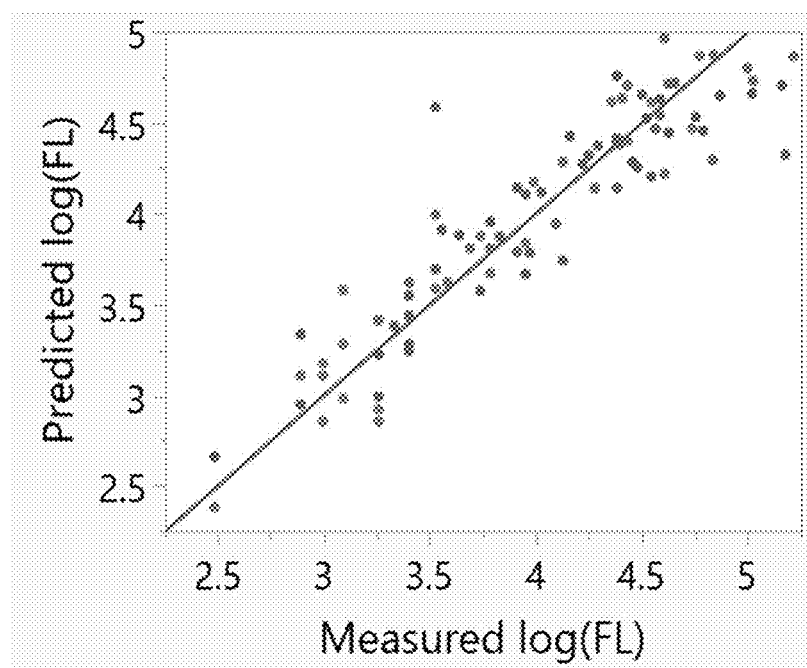
FIG. 7 is a parity plot of fluid loss for a fluid loss experiment.

A series of static fluid loss tests were performed according to API RP Practice 10B-2 for various cement fluid loss control additives the fluid loss for each fluid loss control additive was determined. A parity plot was created from the observed fluid loss to predicted fluid loss and is shown in FIG. 7. It can be observed from FIG. 7 that the model predictions of fluid loss can successfully describe the fluid loss behavior of a different types of cement fluid loss control additives.

The disclosed cement slurries and associated methods may directly or indirectly affect any pumping systems, which representatively includes any conduits, pipelines, trucks, tubulars, and/or pipes which may be coupled to the pump and/or any pumping systems and may be used to fluidically convey the cement slurries downhole, any pumps, compressors, or motors (e.g., topside or downhole) used to drive the cement slurries into motion, any valves or related joints used to regulate the pressure or flow rate of the cement slurries, and any sensors (i.e., pressure, temperature, flow rate, etc.), gauges, and/or combinations thereof, and the like. The cement slurries may also directly or indirectly affect any mixing hoppers and retention pits and their assorted variations.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

For the sake of brevity, only certain ranges are explicitly disclosed herein. However, ranges from any lower limit may be combined with any upper limit to recite a range not explicitly recited, as well as ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular examples disclosed above are illustrative only, as the present disclosure may be modified and practiced in different but equivalent manners apparent to those skilled in the art having the benefit of the teachings herein. Although individual examples are discussed, the disclosure covers all combinations of all those examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method of designing a cement slurry comprising:
   (a) selecting at least a cementitious material and concentration thereof, a water and concentration thereof, and a fluid loss control additive and concentration thereof to form a cement slurry recipe;
   (b) calculating a fluid loss of the cement slurry recipe using a fluid loss model, wherein the fluid loss model comprises an equation of the following form:

$$FL = \left(\sum_i FL_0^i P_i\right)\left(\frac{w}{\sum_i \alpha_i P_i}\right)^n \exp(\gamma C)$$

where FL is fluid loss, $FL_0^i$ is a constant for each cementitious material i in the cement slurry, $P_i$ is concentration of cementitious material i in the cement slurry recipe, w is amount of water in the cement slurry recipe, $\alpha_i$ is a constant, $\gamma$ is a measure of effectiveness of fluid loss control additive, n is a constant, and C is a concentration of fluid loss control additive in the cement slurry recipe;
   (c) comparing the fluid loss of the cement slurry recipe to a fluid loss requirement, wherein steps (a)-(c) are repeated if the fluid loss of the cement slurry recipe does not meet or stay below the fluid loss requirement, wherein each repeated step of selecting comprises selecting different concentrations and/or different chemical identities for the fluid loss control additive, cementitious material, or water than previously selected, or step (d) is performed if the fluid loss of the cement slurry recipe meets or stays below the fluid loss requirement;
   (d) preparing a cement slurry based on the cement slurry recipe, wherein the cement slurry has the property of having fluid loss at or below the fluid loss requirement; and
   (e) introducing the cement slurry into a subterranean formation, wherein the cement slurry sets to form a hardened mass.

2. The method of claim 1 wherein the cement slurry recipe further comprises one or more additives is selected from the group consisting of weighting agents, lightweight additives, gas-generating additives, mechanical-property-enhancing additives, lost-circulation control materials, filtration-control additives, defoaming agents, foaming agents, thixotropic additives, dispersants, suspending aids, viscosifiers, transition time control additives and combinations thereof.

3. The method of claim 1 wherein the fluid loss model comprises an equation of the following form:

$$FL = FL_0 h(w,P) * \exp(\gamma C)$$

where FL is fluid loss, $FL_0$ is a constant, $\gamma$ is a measure of effectiveness of fluid loss control additive, C is a concentration of fluid loss control additive, h( ) is a function, w amount of water and P is amount of cementitious material or the sum amount of the cementitious materials ($P_i$) when more than one cementitious material is present.

4. The method of claim 3, wherein h( ) is at least one of a polynomial function, power law function, exponential function, logarithmic function, trigonometric function, transcendental function, analytic expression, a neural net, a decision tree, or a combination thereof.

5. The method of claim 1 wherein the fluid loss model further comprises an equation of the following form:

$$FL = FL_0 * g(C_i)$$

where FL is fluid loss $FL_0$ is a constant $C_i$ is concentration of fluid loss control additive and g( ) is at least one of a polynomial function, power law function, exponential function, logarithmic function, trigonometric function, transcendental function, analytic expression, a neural net, a decision tree, or a combination thereof.

6. The method of claim 1 wherein the fluid loss model further comprises an equation of the following form:

$$FL = FL_0 * 1/(1+\beta C_i)$$

where FL is fluid loss $FL_0$ is a constant $C_i$ is concentration of fluid loss control additive, and b is a constant associated with physico-chemical properties of the fluid loss control additive.

7. The method of claim 1 wherein the fluid loss model further comprises an equation of the following form:

$$FL = FL_0 * \exp(-\beta C_i)$$

where FL is fluid loss $FL_0$ is a constant $C_i$ is concentration of fluid loss control additive, and b is a constant associated with physico-chemical properties of the fluid loss control additive.

8. The method of claim 1 further comprising placing the cement slurry in a subterranean formation.

9. A method comprising:
   (a) providing a fluid loss model;
   (b) providing a fluid loss requirement;
   (c) generating a cement slurry recipe using the fluid loss model and the fluid loss requirement such that a calculated fluid loss of the cement slurry recipe using the fluid loss model meets or stays below the fluid loss requirement, wherein the fluid loss model comprises an equation of the following form:

$$FL = \left(\sum_i FL_0^i P_i\right)\left(\frac{w}{\sum_i \alpha_i P_i}\right)^n \exp(\gamma C)$$

where FL is fluid loss, $FL_0^i$ is a constant for each cementitious material i in the cement slurry, $P_i$ is concentration of cementitious material i, w is amount of water, $\alpha_i$ is a constant, $\gamma$ is a measure of effectiveness of fluid loss control additive, and C is a concentration of fluid loss control additive;

(d) preparing a cement slurry based on the cement slurry recipe, wherein the cement slurry has the property of having fluid loss at or below the fluid loss requirement; and (e) introducing the cement slurry into a subterranean formation, wherein the cement slurry sets to form a hardened mass.

10. The method of claim 9 wherein the fluid loss model further comprises an equation of the following form:

$$FL=FL_0*g(C_i)$$

where FL is fluid loss $FL_0$ is a constant $C_i$ is concentration of fluid loss control additive and g( ) is at least one of a polynomial function, power law function, exponential function, logarithmic function, trigonometric function, transcendental function, analytic expression, a neural net, a decision tree, or a combination thereof.

11. The method of claim 9 wherein the fluid loss model further comprises an equation of the following form:

$$FL=FL_0*1/(1+\beta C_i)$$

where FL is fluid loss $FL_0$ is a constant $C_i$ is concentration of fluid loss control additive, and b is a constant associated with physico-chemical properties of the fluid loss control additive.

12. The method of claim 9 wherein the fluid loss model further comprises an equation of the following form:

$$FL=FL_0*\exp(-\beta C_i)$$

where FL is fluid loss $FL_0$ is a constant $C_i$ is concentration of fluid loss control additive, and b is a constant associated with physico-chemical properties of the fluid loss control additive.

13. The method of claim 9 further comprising introducing the cement slurry in a subterranean formation.

14. A method of designing a cement slurry comprising:
(a) selecting at least a cementitious material and concentration thereof, a water and concentration thereof, and a fluid loss control additive and concentration thereof to form a cement slurry recipe;
(b) calculating a fluid loss of the cement slurry recipe using a fluid loss model, wherein the fluid loss model comprises an equation of the following form:

$$FL = FL_0 \exp\left(-\frac{E}{RT}\right)\exp(-V_0 P_r)\left(\frac{w}{P}\right)^n * \exp(\gamma C)$$

where FL is fluid loss $FL_0$ is a constant, $\gamma$ is a measure of effectiveness of fluid loss control additive in the cement slurry recipe, C is a concentration of fluid loss control additive in the cement slurry recipe, E is activation energy, $V_0$ is activation volume, T is temperature, $P_r$ is pressure differential, R is universal gas constant, w is amount of water, and P is amount of cementitious material or the sum amount of the cementitious materials ($P_i$) when more than one cementitious material is present in the cement slurry recipe;

(c) comparing the fluid loss of the cement slurry recipe to a fluid loss requirement, wherein steps (a)-(c) are repeated if the fluid loss of the cement slurry recipe does not meet or stay below the fluid loss requirement, wherein each repeated step of selecting comprises selecting different concentrations and/or different chemical identities for the fluid loss control additives, cementitious material, or water than previously selected, or step (d) is performed if the fluid loss of the cement slurry recipe meets or stays below the fluid loss requirement;

(d) preparing a cement slurry based on the cement slurry recipe, wherein the cement slurry has the property of having fluid loss at or below the fluid loss requirement; and (e) introducing the cement slurry into a subterranean formation, wherein the cement slurry sets to form a hardened mass.

15. A method of designing a cement slurry comprising:
(a) selecting at least a cementitious material and concentration thereof, a water and concentration thereof, and a fluid loss control additive and concentration thereof to form a cement slurry recipe;
(b) calculating a fluid loss of the cement slurry recipe using a fluid loss model, wherein the fluid loss model comprises an equation of the following form:

$$FL = (FL_1 P_1 + FL_2 P_2 + FL_{12} P_1 P_2)\left(\frac{w}{P}\right) * \exp(\gamma C)$$

where FL is fluid loss, $FL_1$ and $FL_2$ are fluid loss coefficients for cement and chemical additive, $P_1$ and $P_2$ are concentrations of cement and chemical additive in the cement slurry recipe, $FL_{12}$ is an interaction coefficient, w is amount of water in the cement slurry recipe, P is the amount of cementitious material or the sum amount of the cementitious materials ($P_i$) when more than one cementitious material is present in the cement slurry recipe, $\gamma$ is a measure of effectiveness of fluid loss control additive, and C is a concentration of fluid loss control additive in the cement slurry recipe;

(c) comparing the fluid loss of the cement slurry recipe to a fluid loss requirement, wherein steps (a)-(c) are repeated if the fluid loss of the cement slurry recipe does not meet or stay below the fluid loss requirement, wherein each repeated step of selecting comprises selecting different concentrations and/or different chemical identities for the one or more fluid loss control additives, cementitious material, or water than previously selected, or step (d) is performed if the fluid loss of the cement slurry recipe meets or stays below the fluid loss requirement;

(d) preparing a cement slurry based on the cement slurry recipe, wherein the cement slurry has the property of having fluid loss at or below the fluid loss requirement; and (e) introducing the cement slurry into a subterranean formation, wherein the cement slurry sets to form a hardened mass.

16. A method comprising:
(a) providing a fluid loss model;
(b) providing a fluid loss requirement;

(c) generating a cement slurry recipe using the fluid loss model and the fluid loss requirement such that a calculated fluid loss of the cement slurry recipe using the fluid loss model meets or stays below the fluid loss requirement, wherein the fluid loss model comprises an equation of the following form:

$$FL = FL_0 \exp\left(-\frac{E}{RT}\right) \exp(-V_0 P_r)\left(\frac{w}{P}\right)^n * \exp(\gamma C)$$

where FL is fluid loss $FL_0$ is a constant, $\gamma$ is a measure of effectiveness of fluid loss control additive, C is a concentration of fluid loss control additive in the cement slurry recipe, E is activation energy, $V_0$ is activation volume, T is temperature, $P_r$ is pressure differential, R is universal gas constant, w is amount of water, and P is amount of cementitious material or the sum amount of the cementitious materials ($P_i$) when more than one cementitious material is present in the cement slurry recipe;

(d) preparing a cement slurry based on the cement slurry recipe, wherein the cement slurry has the property of having fluid loss at or below the fluid loss requirement; and (e) introducing the cement slurry into a subterranean formation, wherein the cement slurry sets to form a hardened mass.

17. A method comprising:
(a) providing a fluid loss model;
(b) providing a fluid loss requirement;
(c) generating a cement slurry recipe using the fluid loss model and the fluid loss requirement such that a calculated fluid loss of the cement slurry recipe using the fluid loss model meets or stays below the fluid loss requirement, wherein the fluid loss model comprises an equation of the following form:

$$FL = (FL_1 P_1 + FL_2 P_2 + FL_{12} P_1 P_2)\left(\frac{w}{P}\right) * \exp(\gamma C)$$

where FL is fluid loss, $FL_1$ and $FL_2$ are fluid loss coefficients for cement and chemical additive, $P_1$ and $P_2$ are concentrations of cement and chemical additive in the cement slurry recipe, $FL_{12}$ is an interaction coefficient, w is amount of water, P is the amount of cementitious material or the sum amount of the cementitious materials ($P_i$) when more than one cementitious material is present, $\gamma$ is a measure of effectiveness of fluid loss control additive, and C is a concentration of fluid loss control additive in the cement slurry recipe;

(d) preparing a cement slurry based on the cement slurry recipe, wherein the cement slurry has the property of having fluid loss at or below the fluid loss requirement; and (e) introducing the cement slurry into a subterranean formation, wherein the cement slurry sets to form a hardened mass.

* * * * *